US011998660B2

(12) United States Patent
Kelly et al.

(10) Patent No.: US 11,998,660 B2
(45) Date of Patent: Jun. 4, 2024

(54) METHOD FOR MAKING A POROUS SCAFFOLD SUITABLE FOR USE IN REPAIR OF OSSEOUS, CHONDRAL, OR OSTEOCHONDRAL DEFECTS IN A MAMMAL

(71) Applicant: THE PROVOST, FELLOWS, SCHOLARS AND OTHER MEMBERS OF BOARD OF TRINITY COLLEGE DUBLIN, Dublin (IE)

(72) Inventors: Daniel John Kelly, Dublin (IE); Grainne Cunniffe, Dublin (IE); Henrique Almeida, Dublin (IE); Rajalakshmanan Eswaramoorthy, Dublin (IE); Conor Buckley, Dublin (IE); Pedro Jose Diaz Payno, Dublin (IE); David Browe, Dublin (IE)

(73) Assignee: THE PROVOST, FELLOWS, SCHOLARS AND OTHER MEMBERS OF BOARD OF TRINITY COLLEGE DUBLIN, Dublin (IE)

(*) Notice: Subject to any disclaimer, the term of this patent is extended or adjusted under 35 U.S.C. 154(b) by 0 days.

(21) Appl. No.: 16/795,770

(22) Filed: Feb. 20, 2020

(65) Prior Publication Data
US 2020/0188556 A1 Jun. 18, 2020

Related U.S. Application Data

(62) Division of application No. 15/502,633, filed as application No. PCT/EP2015/068855 on Aug. 17, 2015, now abandoned.

(30) Foreign Application Priority Data
Aug. 15, 2014 (EP) .................................. 14181154.7

(51) Int. Cl.
A61L 27/50 (2006.01)
A61L 27/36 (2006.01)
(Continued)

(52) U.S. Cl.
CPC ....... *A61L 27/3633* (2013.01); *A61L 27/3612* (2013.01); *A61L 27/365* (2013.01);
(Continued)

(58) Field of Classification Search
CPC ........... A61L 2300/414; A61L 2300/64; A61L 2430/02; A61L 2430/06; A61L 2430/40;
(Continued)

(56) References Cited

U.S. PATENT DOCUMENTS 4,488,911 A * 12/1984 Luck ..................... A61L 15/325
106/151.1
5,158,574 A * 10/1992 Stone ...................... A61L 27/24
264/108
(Continued)

FOREIGN PATENT DOCUMENTS

WO 2001045764 A1 6/2001
WO WO-2008109407 A2 * 9/2008 ............. A61L 27/54
(Continued)

OTHER PUBLICATIONS

Saldin et al. (Acta Biomater. 2017;49:1-15). (Year: 2017).*
(Continued)

*Primary Examiner* — Ernst V Arnold
(74) *Attorney, Agent, or Firm* — Nixon Peabody LLP; David S. Resnick; Nicole D. Kling

(57) ABSTRACT

A method for making a porous devitalised scaffold suitable for use in repair of osseous, chondral, or osteochondral defects in a mammal comprises the steps of providing micronized extracellular matrix (ECM) tissue, mixing the micronized extracellular matrix with a liquid to provide a
(Continued)

slurry, and freeze-drying the slurry to provide the porous scaffold. A porous scaffold suitable for use in repair of osseous, chondral, or osteochondral defects in a mammal and comprising a porous freeze-dried matrix formed from micronised decellularised extracellular matrix tissue is also described.

19 Claims, 14 Drawing Sheets

(51) Int. Cl.
*A61L 27/38* (2006.01)
*A61L 27/44* (2006.01)
*A61L 27/52* (2006.01)
*A61L 27/54* (2006.01)
*A61L 27/56* (2006.01)
*A61L 27/58* (2006.01)

(52) U.S. Cl.
CPC ....... *A61L 27/3654* (2013.01); *A61L 27/3683* (2013.01); *A61L 27/3691* (2013.01); *A61L 27/3695* (2013.01); *A61L 27/3817* (2013.01); *A61L 27/3821* (2013.01); *A61L 27/3847* (2013.01); *A61L 27/3852* (2013.01); *A61L 27/44* (2013.01); *A61L 27/52* (2013.01); *A61L 27/54* (2013.01); *A61L 27/56* (2013.01); *A61L 2300/414* (2013.01); *A61L 2300/64* (2013.01); *A61L 2430/02* (2013.01); *A61L 2430/06* (2013.01); *A61L 2430/40* (2013.01)

(58) Field of Classification Search
CPC ............. A61L 27/3612; A61L 27/3633; A61L 27/365; A61L 27/3654; A61L 27/3683; A61L 27/3691; A61L 27/3817; A61L 27/3821; A61L 27/3847; A61L 27/54; A61L 27/56
See application file for complete search history.

(56) References Cited

U.S. PATENT DOCUMENTS

2003/0095994 A1* 5/2003 Geistlich ................. A61P 19/02
424/426
2007/0113951 A1 5/2007 Huang
2014/0369984 A1* 12/2014 Murray ............... A61L 27/3804
424/93.73

FOREIGN PATENT DOCUMENTS

WO 2010083051 A2 7/2010
WO WO-2010084481 A1 * 7/2010 ................ A61F 2/02

OTHER PUBLICATIONS

Wang et al. (Acta Biomaterialia 2011;7:2410-2417) (Year: 2011).*
Schwarz et al. (Tissue Engineering 2012; 18(21 and 22):2195-2209) (Year: 2012).*
Haugh et al. (J. Biomed. Mater. Res. 2009;89A:363-369) (Year: 2009).*
"Oral Presentations" Journal of Tissue Engineering and Regenerative Medicine 8: 39-206 (2014).
"Poster Presentations" Journal of Tissue Engineering and Regenerative Medicine 8: 207-518 (2014).
Almeida et al., "Controlled release of transforming growth factor-β3 from cartilage-extra-cellular-matrix-derived scaffolds to promote chondrogenesis of human-joint-tissue-derived stem cells." Acta biomaterialia 10(10): 4400-4409 (2014).
Almeida et al., "Coupling Freshly Isolated CD44+ Infrapatellar Fat Pad-Derived Stromal Cells with a TGF-β3 Eluting Cartilage ECM-Derived Scaffold as a Single-Stage Strategy for Promoting Chondrogenesis." Advanced Healthcare Materials 4(7): 1043-1053 (2015).
Ameida et al., "Optimizing cartilage extracellular matrix derived scaffolds to act as growth factor delivery platforms to promote chondrogenesis of mesenchymal stem cell" European Cells and Materials 26(8): 6 (2013).
Haugh et al., "Crosslinking and mechanical properties significantly influence cell attachment, proliferation, and migration within collagen glycosaminoglycan scaffolds." Tissue Engineering Part A 17(9-10): 1201-1208 (2011).
Kheir et al., "Development and characterization of an acellular porcine cartilage bone matrix for use in tissue engineering." Journal of Biomedical Materials Research Part A 99(2): 283-294 (2011).
Liu et al. "[Preparation and biocompatibility evaluation of novel cartilage acellular matrix sponge]." Zhongguo Xiu Fu Chong Jian Wai Ke Za Zhi = Zhongguo Xiufu Chongjian Waike Zazhi = Chinese Journal of Reparative and Reconstructive Surgery 23(8): 1002-1006 (2009) [Abstract].
Matsiko et al., "Addition of hyaluronic acid improves cellular infiltration and promotes early-stage chondrogenesis in a collagen-based scaffold for cartilage tissue engineering." Journal of the Mechanical Behavior of Biomedical Materials 11: 41-52 (2012).
Schwarz et al., "Decellularized cartilage matrix as a novel biomatrix for cartilage tissue-engineering applications." Tissue Engineering Part A 18(21-22): 2195-2209 (2012).
Fermandez-Perez et al. "The impact of decellularization methods on extracellular matrix derived hydrogels." Scientific Reports 9.1 (2019): 1-12.
Lange et al. "Pilot study of a novel vacuum-assisted method for decellularization of tracheae for clinical tissue engineering applications." Journal of tissue engineering and regenerative medicine 11.3 (2017): 800-811.
Vas et al. "Decellularized cartilage directs chondrogenic differentiation: Creation of a fracture callus mimetic." Tissue Engineering Part A 24.17-18 (2018): 1364-1376.

* cited by examiner

METHOD FOR MAKING A POROUS SCAFFOLD SUITABLE FOR USE IN REPAIR OF OSSEOUS, CHONDRAL, OR OSTEOCHONDRAL DEFECTS IN A MAMMAL

CROSS-REFERENCE TO RELATED APPLICATIONS

This application is a divisional under 35 U.S.C. § 121 of U.S. Ser. No. 15/502,633 filed Feb. 8, 2017 now abandoned, which is a 35 U.S.C. § 371 National Phase Entry application of International Application No. PCT/EP15/068855 filed Aug. 17, 2015 which designates the U.S. and claims priority to and benefit under 35 U.S.C. § 119(a) of European Application No. 14181154.7 filed Aug. 15, 2014, the contents of which are incorporated herein by reference in their entirety.

INTRODUCTION

The invention relates to a method for making a porous scaffold suitable for use in repair of osseous, chondral, or osteochondral defects in a mammal. The invention also relates to a porous scaffold suitable for use in repair of osseous, chondral, or osteochondral defects in a mammal, and a multilayer scaffold suitable for use in repair of osteochondral defects in a mammal.

In humans, 95% of defects to the articular surface of synovial joints involve cartilage without affecting the subchondral bone (Hjelle et al., 2002). Such defects fail to heal spontaneously. An estimated 5.4 million patients in the US alone will require joint and cartilage procedures to treat such defects and other degenerative changes by 2019. Bone marrow stimulation techniques such as microfracture are the most readily available clinical repair strategies for articular cartilage (Getgood et al., 2009). By surgically penetrating the subchondral bone, progenitor cells from the bone marrow can migrate into the defect and form a repair tissue. In general, a mechanically inferior fibro-cartilaginous tissue is produced which provides only temporary symptomatic relief. Alternative cell based therapies such as autologous chondrocytes implantation (ACI) are available, however these approaches require two hospital stays and are very expensive (~€35,000), which may explain their relatively limited clinical uptake compared to marrow stimulation techniques. There is therefore a significant commercial opportunity for a cost effective 'single-stage' or 'in-theatre' therapy (such as the proposed scaffold) for regenerating damaged articular cartilage.

Scaffolds fabricated using decellularized extracellular matrix (ECM) have shown great promise for the regeneration of damaged tissues. This approach has been used to develop different tissue-specific (e.g. heart valves, blood vessels, skin and cartilage) scaffolds. In the case of articular cartilage, numerous studies have demonstrated that scaffolds derived from devitalized cartilage are chondroinductive and show great promise for regenerating damaged joints. There are, however, a number of limitations associated with current ECM derived scaffolds, including inhomogeneous pore size with current cartilage ECM derived scaffolds (which limits cellular infiltration into the scaffold and leads to inhomogenous deposition of matrix within the scaffold), failure to generate hyaline cartilage within the scaffold or a defect treated with the scaffold, poor control over scaffold pore size, inefficient decellularization of ECM prior to scaffold fabrication, variability in scaffold composition which impacts commercial production, and poor control of the release of exogenous growth factors loaded onto ECM derived scaffolds. Furthermore, it remains unclear how ECM derived scaffolds can be used to treat defects that effect multiple different tissues such as osteochondral defects".

It is an object of the invention to overcome at least one of the above-referenced problems.

STATEMENTS OF INVENTION

The Applicant has discovered that freeze-drying a slurry of micronized extracellular matrix (ECM) tissue derived from hyaline cartilage (preferably articular cartilage) or growth plate tissue provides scaffolds having a homogenous pore size (FIG. 1) that demonstrate a high level of homogenous stem cell infiltration in-vitro (FIG. 2) and a high level of deposition of cartilage-like extracellular matrix (FIG. 3). The Applicant has successfully employed decellularization techniques in order to sufficiently reduce xenogeneic DNA from the scaffolds (FIG. 8).

Cartilage extracellular matrix consists primarily of glycosaminoglycans (GAG) and type II collagen. The Applicant has discovered that by reducing the glycosaminoglycan content of the cartilage ECM using a detergent or similar (FIG. 8), and hence increasing the ratio of collagen to GAG within the treated ECM, improves the resultant capacity of the scaffold to induce robust chondrogenesis after they have been seeded with mesenchymal stem cells (FIGS. 9 and 10). The Applicant has also discovered that crosslinking the scaffolds of the invention slows growth factor release from the scaffolds (FIG. 4), and that reducing the glycosaminoglycan content of the scaffolds of the invention also slows growth factor release from the scaffold (FIG. 7). The Applicant has also discovered that scaffolds formed from micronized growth plate ECM generates extensive mineralisation of cranial and femoral defects (FIGS. 23 and 24) and enhanced bone tissue formation (FIG. 25), and that growth plate ECM derived scaffolds that are seeded with mesenchymal stem cells support endochondral bone formation in chondrogenic conditions in vitro (FIGS. 19-21).

The Applicant has also discovered that treated or native ECM can be solubilised by solubilisation of the ECM. After solubilisation the ECM can then be cross-linked and freeze-dried to create scaffolds. The solubilisation process employed removes the vast majority of GAG and residual xenogeneic DNA from the resulting scaffold. (FIG. 25).

Accordingly, in a first aspect, the invention provides a method for making a porous scaffold suitable for use in repair of osseous, chondral, or osteochondral defects in a mammal, the method comprising the step of:
  providing a slurry of micronized extracellular matrix (ECM) tissue or a gel comprising solubilised and crosslinked extracellular matrix (ECM) tissue; and
  freeze-drying the slurry or gel to provide the porous scaffold.

Thus, the ECM material that is freeze-dried may be a slurry formed from micronized ECM or it may be a gel formed by solubilisation of ECM (optionally micronized ECM) that is cross-linked, typically chemically cross-linked, to form a gel prior to freeze-drying. Preferably, the solution of enzymatically digested ECM is cross-linked prior to freeze-drying.

In one embodiment, the ECM is solubilised by enzymatic digestion. In one embodiment, the ECM is micronized prior to solubilisation.

Preferably, the slurry comprises 100-400 mg/ml micronised ECM tissue, ideally 200-300 mg/ml micronised ECM tissue.

Preferably, the micronized extracellular matrix tissue has a mean particle size of 10-200 microns, ideally 20-70 microns.

Typically, the micronized extracellular matrix tissue is cryomilled extracellular matrix tissue.

Suitably, extracellular matrix is treated to reduce the GAG content. Preferably, the extracellular matrix is treated to reduce the GAG content after the extracellular matrix is micronized.

Typically, the porous scaffold is cross-linked.

Preferably, the extracellular matrix is hyaline cartilage (preferably articular cartilage) ECM or growth plate ECM.

Preferably, the extracellular matrix is decellularised before or after micronizing, ideally after micronisation.

Suitably, the method of the invention includes an additional step of seeding the scaffold with a biological material, for example cells, preferably mesenchymal cells, or a biological molecule, for example a growth factor. This could be achieved by, for example, soaking the prepared scaffold in a solution containing the growth factor or cells of interest. Suitably, the biological material or molecule (biologic) is selected from the groups of: cells; and biological growth factors. Typically, the biological growth factors are selected from the group consisting of one or more of the TGF-β superfamily, (IFG, FGF, BMP, PDGF, EGF) or cannabinoids. These growth factors can also be included during the production process as opposed to post-fabrication soaking of the scaffolds.

In a preferred embodiment, the invention provides a method for making a porous devitalised scaffold suitable for use in repair of osseous, chondral, or osteochondral defects in a mammal, the method comprising the step of:
  providing micronized extracellular matrix (ECM) tissue having a mean particle size of 30-70 microns;
  mixing the micronized extracellular matrix with a liquid to provide a slurry comprising 200-300 mg/ml micronized ECM; and
  freeze-drying the slurry to provide the porous scaffold.

The invention also relates to a method of making a multilayer scaffold comprising the steps of making a first layer comprising a porous scaffold according to a method of the invention, making a second layer comprising a porous scaffold according to a method of the invention, wherein the first layer is attached to the second layer.

Preferably, the process includes a step of attaching the first layer to the second layer to form the multilayer scaffold.

In one embodiment, the first layer comprises ECM from a first source and the second layer comprises ECM from a different source to the first source. Preferably, the first source of ECM is hyaline cartilage ECM and the second source of ECM is growth plate ECM. The latter type of multilayer scaffolds are suitable for repair or treatment of osteochondral defects.

Suitably, the layers are attached together by means of freeze-drying. Thus, for example, the layers may be freeze-dried independently, and then placed in a mould and freeze-dried together. Alternatively, one layer may be freeze-dried and then placed in a mould with a slurry and freeze-dried to form the layered scaffold. Other methods of attaching the two layers include use of adhesives, stitching and intermediate bonding layers.

In a preferred embodiment, the invention also to a method of making a multilayer scaffold comprising the steps of making a first layer comprising a porous scaffold according to a method of the invention in which the ECM is cartilage ECM, making a second layer comprising a porous scaffold according to a method of the invention in which the ECM is growth plate ECM, wherein the first layer is attached to the second layer.

The invention also relates to a porous scaffold formed according to a method of the invention.

The invention also relates to a porous multilayer scaffold formed according to a method of the invention.

The invention also provides a porous scaffold typically suitable for use in repair of osseous, chondral, or osteochondral defects in a mammal and comprising a porous freeze-dried matrix formed from micronised decellularised extracellular matrix or solubilised and crosslinked extracellular matrix.

Preferably, the micronized extracellular matrix tissue has a mean particle size of 10-200 microns, ideally 20-70 microns.

Typically, the micronized extracellular matrix tissue is cryomilled extracellular matrix tissue.

Suitably, extracellular matrix comprises reduced GAG content.

Typically, the porous scaffold is cross-linked.

Preferably, the extracellular matrix is hyaline cartilage ECM (ideally articular cartilage ECM) or growth plate ECM.

Preferably, the micronised extracellular matrix is decellularised.

Suitably, the porous scaffold is seeded with a biological material, for example cells, preferably mesenchymal stem cells, or a biological molecule. Preferably, the ECM is growth plate or hyaline cartilage ECM, and the porous scaffold is seeded with cells, preferably mesenchymal stem cells.

The invention also provides a porous scaffold according to the invention suitable for use in repair of chondral defects in a mammal, in which the extracellular matrix is hyaline (ideally articular) cartilage extracellular matrix.

The invention also provides a porous scaffold according to the invention suitable for use in repair of osseous defects in a mammal, in which the extracellular matrix is growth plate tissue extracellular matrix.

A multilayer scaffold typically suitable for use in repair of osteochondral defects in a mammal and having a first layer comprising a porous scaffold of the invention and a second layer comprising a porous scaffold of the invention, in which the first layer is attached to the second layer.

In one embodiment, the first layer of porous scaffold comprises ECM from a first source and the second layer of porous scaffold comprises ECM from a different source to the first source. Preferably, the first source of ECM is hyaline cartilage ECM and the second source of ECM is growth plate ECM. The latter type of multilayer scaffolds are suitable for repair or treatment of osteochondral defects.

Suitably, the layers are seamlessly attached by means of, for example, freeze-drying. Thus, for example, the layers may be freeze-dried independently, and then placed in a mould and freeze-dried together. Alternatively, one layer may be freeze-dried and then placed in a mould with a slurry and freeze-dried to form the layered scaffold. Other methods of attaching the two layers include use of adhesives, stitching and intermediate bonding layers.

The invention also relates to a porous scaffold or multilayer scaffold of the invention for use in a method of treating osseous, chondral, or osteochondral defects in a mammal, in which the porous scaffold is inserted into the defect.

The invention also relates to a porous scaffold of the invention for use in a method of treating chondral defects in a mammal, in which the porous scaffold comprises cartilage ECM and in which the porous scaffold is inserted into the chondral defect.

The invention also relates to a porous scaffold of the invention for use in treating osseous defects in a mammal, in which the porous scaffold comprises growth plate ECM and in which the porous scaffold is inserted into the osseous defect. The porous scaffold comprises cells, ideally mesenchymal stem cells, although the scaffold may also be cell-free.

The invention also relates to a multilayer scaffold of the invention for use in treating osteochondral defects in a mammal, in which the multilayer scaffold comprises a first layer of porous scaffold comprising hyaline cartilage ECM and a second layer of porous scaffold comprising growth plate ECM, and in which the multilayer scaffold is inserted into the osteochondral defect. The first and/or second layer of porous scaffold may comprise cells, ideally mesenchymal stem cells, although the scaffold is preferably cell-free.

In another aspect, the invention relates to a gel suitable for use in repairing osseous, chondral, or osteochondral defects in a mammal and comprising a gel base and microNised ECM homogenously distributed throughout the gel base.

Typically, the gel base comprises fibrin.

Ideally, the gel is injectable.

The invention also relates to a method of making a gel suitable for use in repairing osseous, chondral, or osteochondral defects in a mammal and comprising the steps of mixing micronised ECM with a gel base. Typically, the process comprises a step of mixing micronised ECM with a liquid gel base precursor, and then adding to the mixture an activator capable of converting the liquid gel base precursor to a gel base. Suitably, the gel base precursor is fibrinogen, the activator is thrombin.

The invention also relates to a method of making a porous devitalised ECM-based scaffold comprising the step of mixing ECM-producing cells within a hydrogel base, culturing the mixture in-vitro such that the ECM-producing cells deposit ECM within the mixture, and then freeze-drying the mixture to provide the porous devitalised ECM-based scaffold.

Typically, the ECM-producing cells are selected from chondrocytes and osteoblasts.

The invention also relates to a porous ECM-based scaffold formed according to the method of the invention.

The invention also relates to a porous ECM-based scaffold formed according to the method of the invention in a micronized form.

The invention also relates to micronized growth plate ECM, a slurry comprising micronized ECM, or a freeze-dried scaffold formed from a slurry of micronized growth plate ECM.

The invention also relates to a porous scaffold formed from micronized, freeze-dried, growth plate ECM.

The invention also relates to a porous freeze-dried scaffold comprising cryomilled ECM.

The invention also relates to a porous scaffold formed from solubilised and crosslinked, freeze-dried, growth plate ECM.

The invention also relates to a porous multilayer scaffold comprising at least first and second layers, the first layer comprising a porous freeze-dried scaffold formed from micronized hyaline cartilage ECM and the second layer comprising a porous freeze-dried scaffold formed from micronized growth plate cartilage ECM.

The invention also relates to a porous growth plate ECM-based scaffold formed according to the method of the invention in a solubilised form.

BRIEF DESCRIPTION OF THE FIGURES

(FIGS. 2A and 2D) 250 mg/ml, (FIGS. 2B and 2E) 500 mg/ml and (FIGS. 2C and 2F) 1000 mg/ml. Picture represents cross-section of ECM derived scaffolds. Poor cellular penetration at day 1 was observed in the (FIG. 2B) 500 mg/ml and (FIG. 2C) 1000 mg/ml scaffolds, which contrasts with the 250 mg/ml scaffold where a homogeneous cellular infiltration was observed (FIG. 2A). At day 28, scaffold with 1000 mg/ml of ECM continued to show poor stem cells infiltration (FIG. 2F).

(FIG. 5A) 5% GAG; (FIG. 5B) 50% GAG; (FIG. 5C) 100% GAG. Mean pore size increased with decreasing GAG concentration.

DETAILED DESCRIPTION OF THE INVENTION

Definitions

Figure 1:
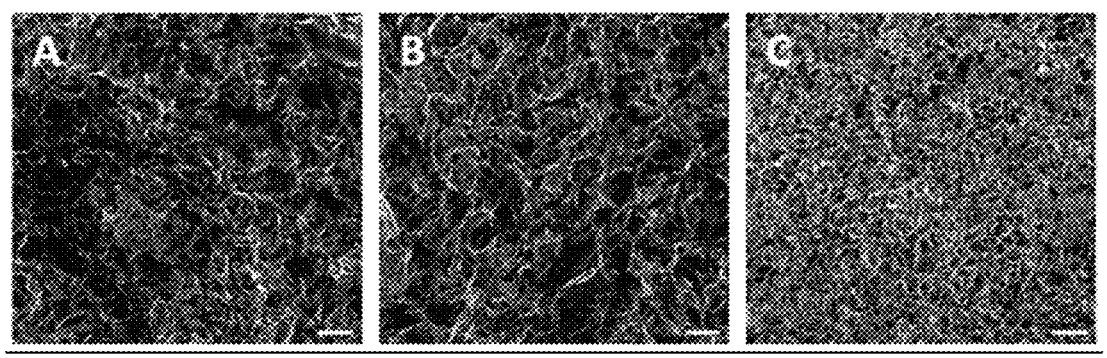
FIG. 1: Concentration modulates scaffold morphology. Helium ion (HIM) micrographs showed different architecture in scaffolds when cartilage ECM slurry concentration was altered: (A) 250 mg/ml; (B) 500 mg/ml; (C) 1000 mg/ml. Mean pore size decreased with increased concentration of ECM.
Figures 2A, 2B, 2C, 2D, 2E, 2F:
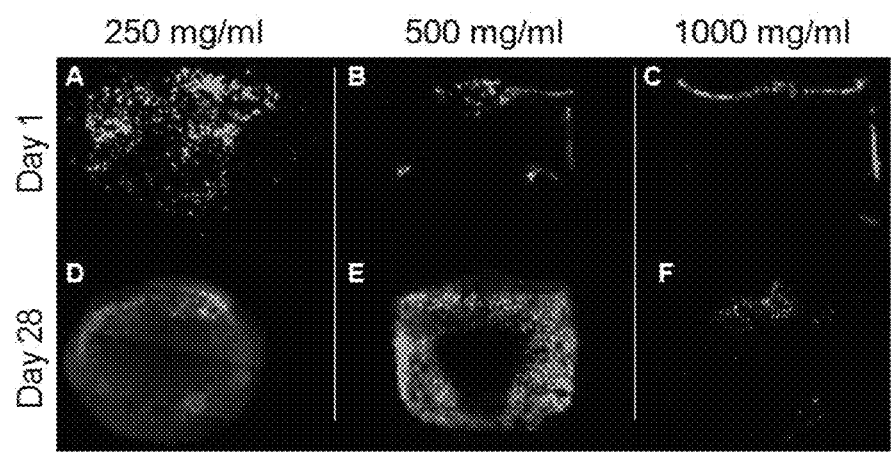
FIGS. 2A-2F: Distribution of live cells. Confocal microscopy at day 1 and day 28 of human infrapatellar fat pad derived stem cells seeded in ECM derived scaffolds.
Figure 3:
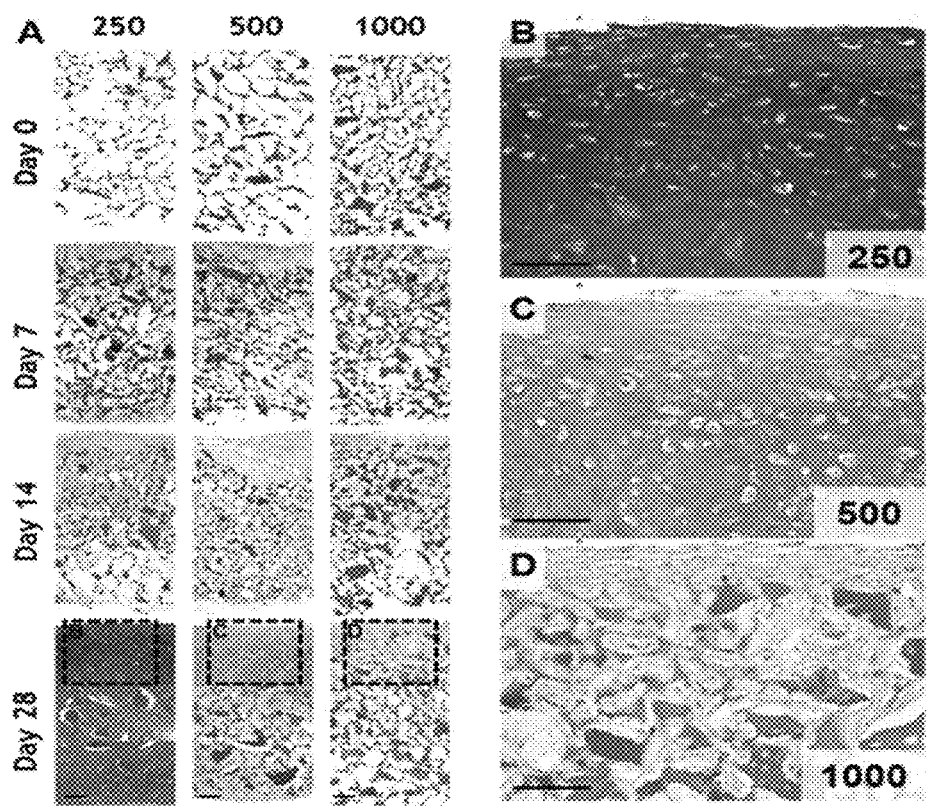
FIG. 3: sGAG deposition for day 0, 7, 14 and 28. Histological images of glycosaminoglycans (GAG) (alcian blue) and cell nuclei (nuclear fast red) staining for ECM derived scaffolds—250, 500 and 1000 mg/ml—at day 0, 7, 14 and 28 of culture (A). In (A) it is possible to observe strong GAG deposition and cell distribution for the 250 mg/ml scaffold. With high magnification it is possible to observe the superior GAG deposition for 250 (B), followed by 500 (C) and 1000 mg/ml scaffold (D).
Figure 4:
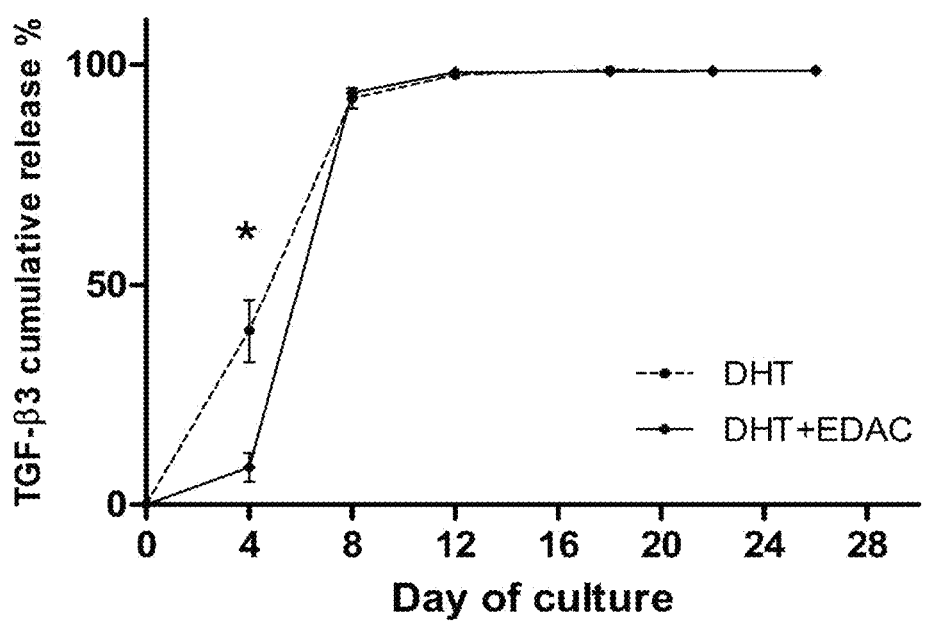
FIG. 4: TGF-β3 release profile for constructs with or without EDAC crosslinking. ELISA results for TGF-β3 release into the media from TGF-β3 loaded ECM derived scaffold indicates slower release rate for scaffolds with EDAC crosslinking, with significant difference at day 4 (n=6, *p<0.05).
Figures 5A, 5B, 5C:
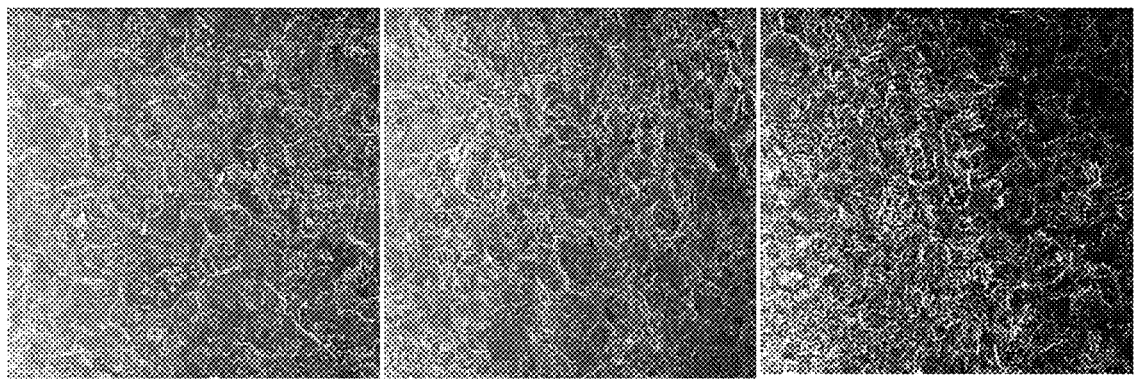
FIGS. 5A-5C: Tailored sGAG scaffold morphology. Helium ion (HIM) micrographs showed altered pore size and architecture in tailoring GAG concentration of scaffolds.
Figure 6:
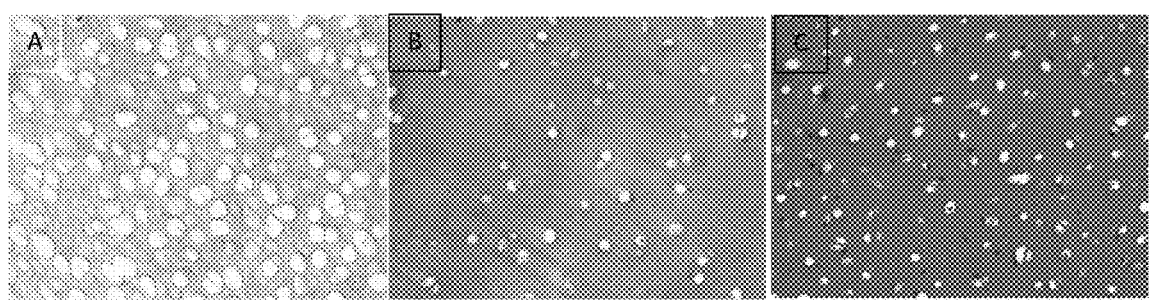
FIG. 6: sGAG Histology. GAG staining on decellularized tailored GAG cartilage explants. micrographs showed in tailoring GAG concentration: (A) 5% GAG; (B) 50% GAG; (C) 100% GAG.
Figure 7:
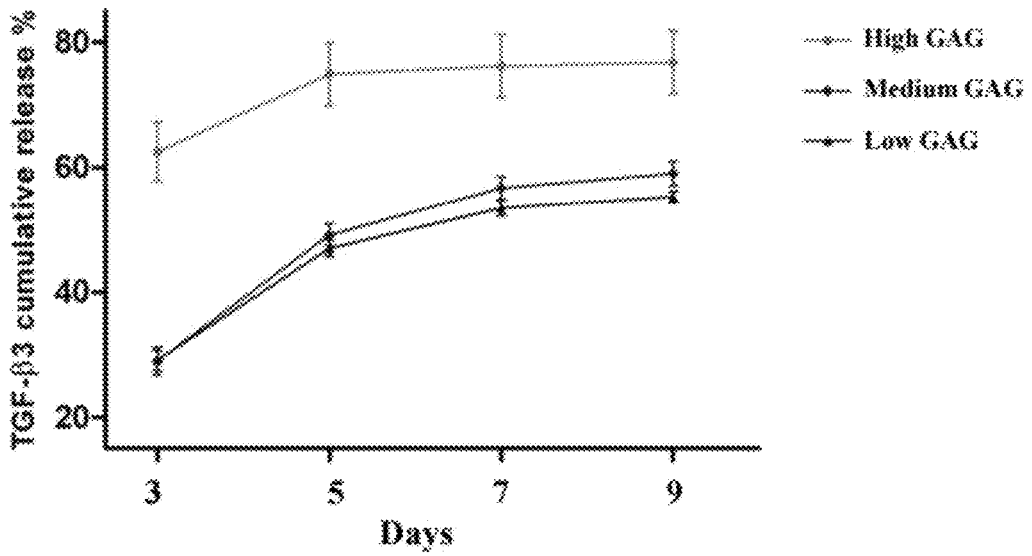
FIG. 7: TGF-β3 release profile from tailored GAG cartilage ECM scaffolds. ELISA results for TGF-β3 release into the media from TGF-β3 loaded ECM derived scaffold 4 (n=4). By removing sGAGs from the ECM prior to scaffold fabrication, it is possible to slow the release of growth factors from the construct.
Figure 8:
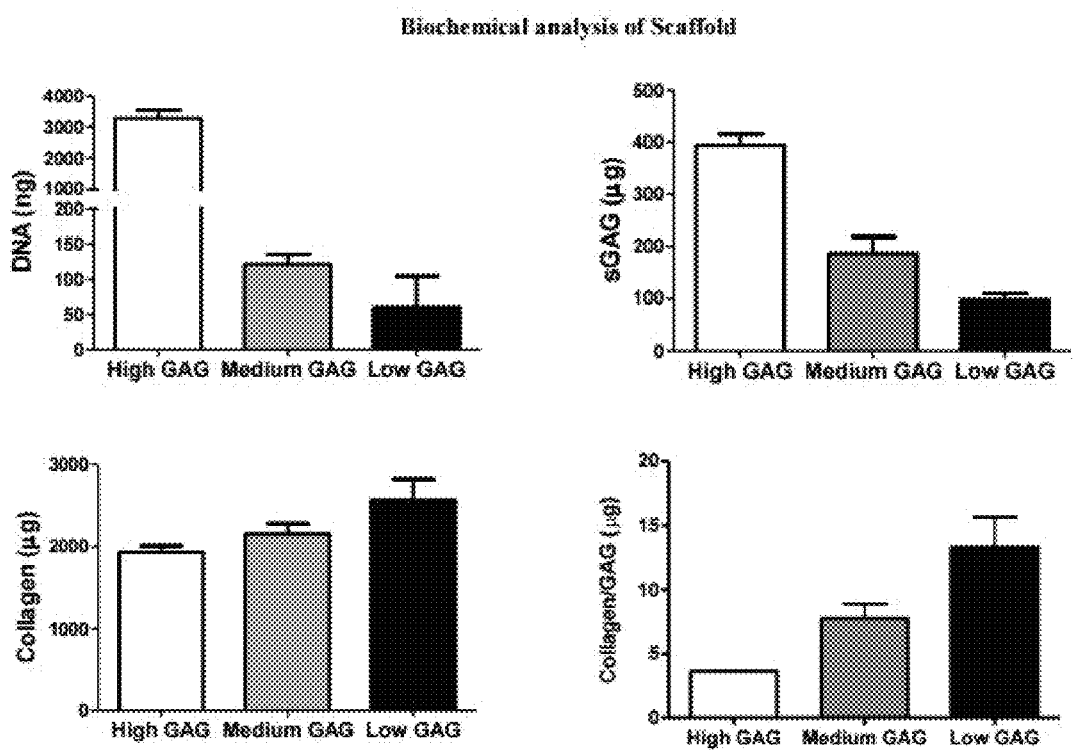
FIG. 8: Biochemical assay for DNA and GAG content of tailored GAG scaffold.
Figure 9:
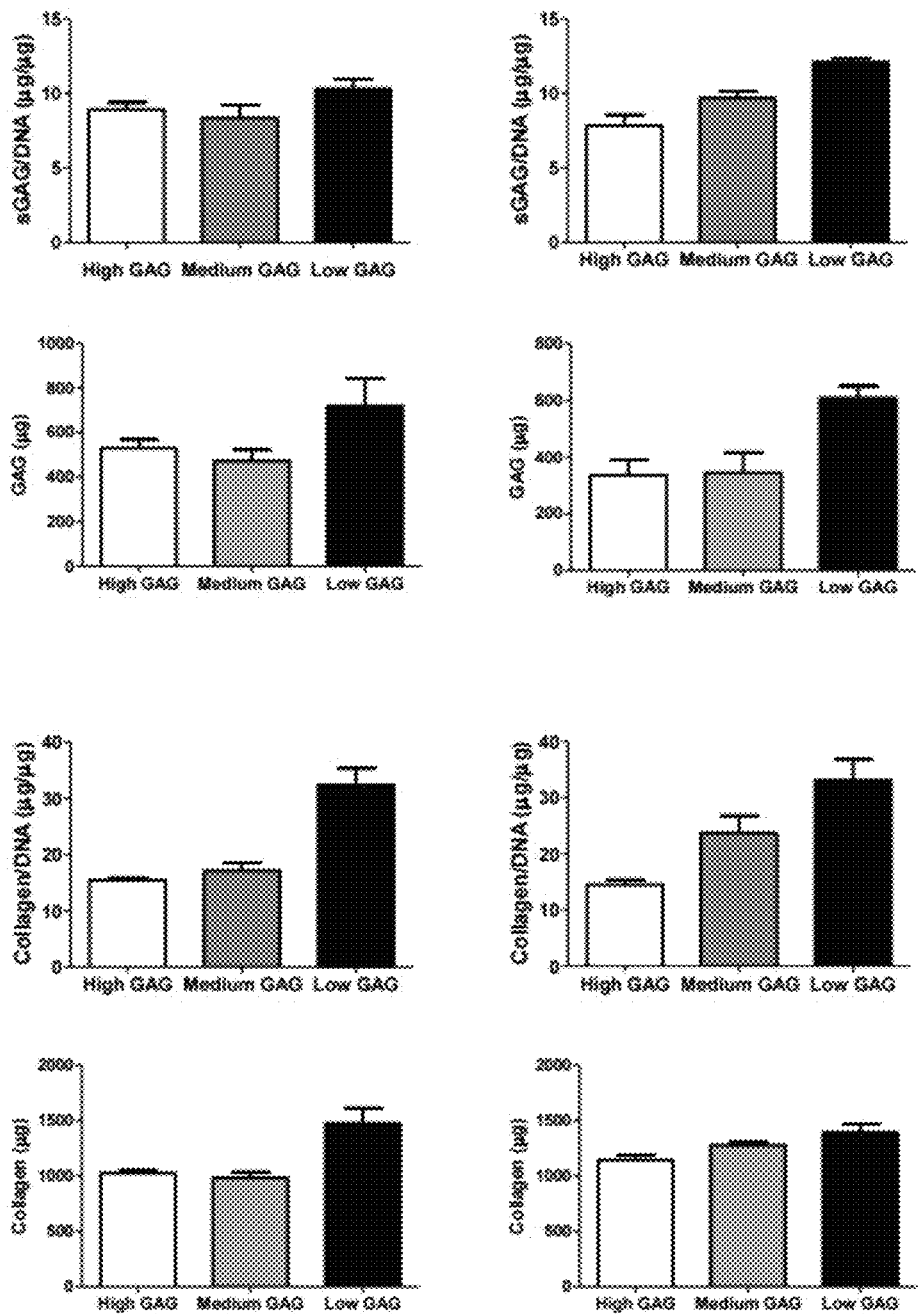
FIG. 9: Biochemical assays performed on cartilage tissues engineered in vitro using tailored GAG scaffolds seeded with human stem cells
Figure 10:
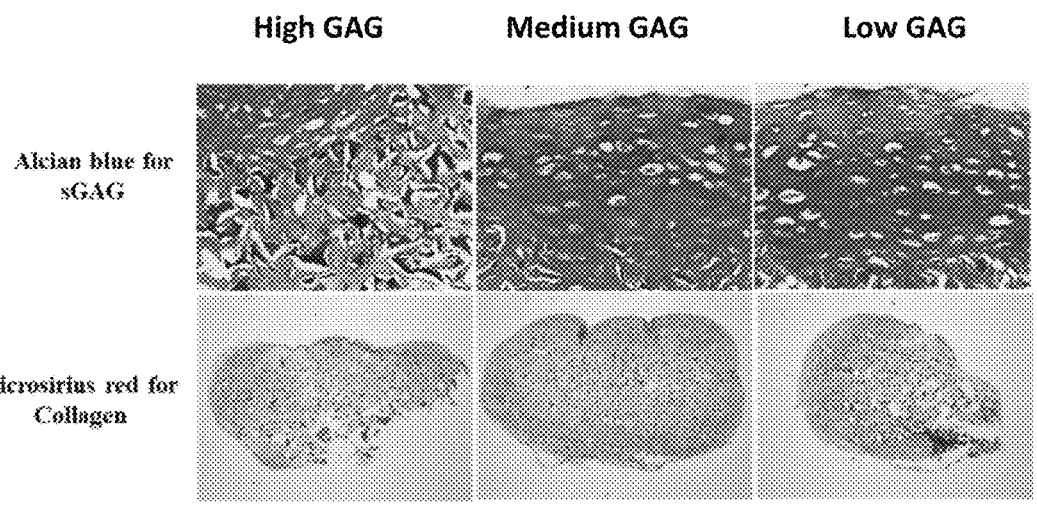
FIG. 10: Histological staining for sGAG (Aldan blue) and Collagen (Picrosirius red) of cartilage tissues engineered in vitro using ECM derived scaffolds seeded with human stem cells.
Figure 11:
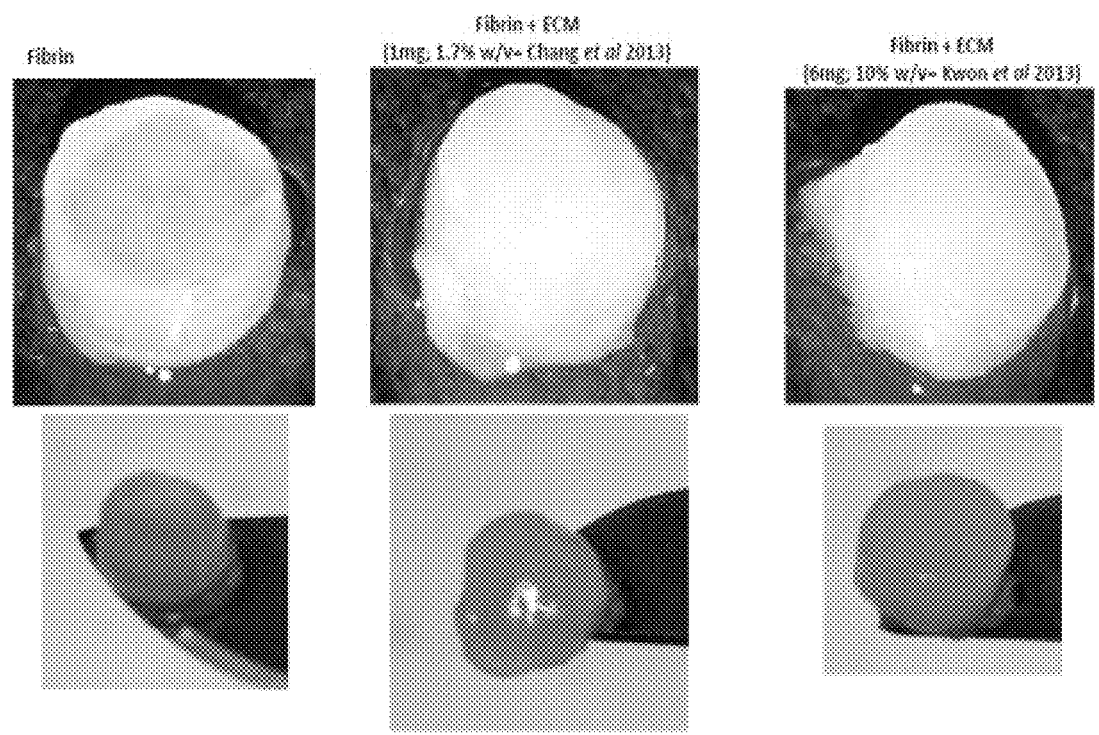
FIG. 11: Gross appearance of Fibrin-ECM particle constructs post-gelation
Figure 12:
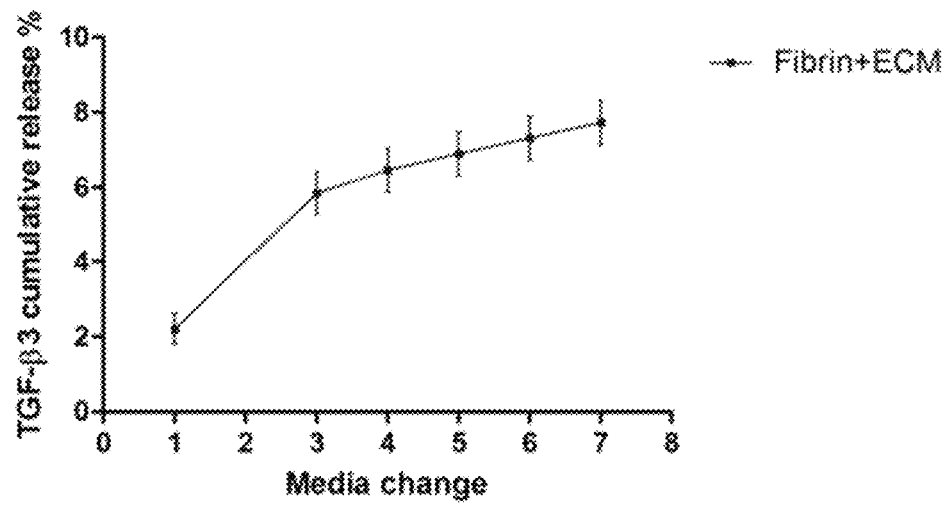
FIG. 12: TGF-β3 release profile for Fibrin hydrogel loaded with ECM particles. ELISA results for TGF-β3 release into the media from TGF-β3 loaded ECM derived particles (n=4).
Figure 13:
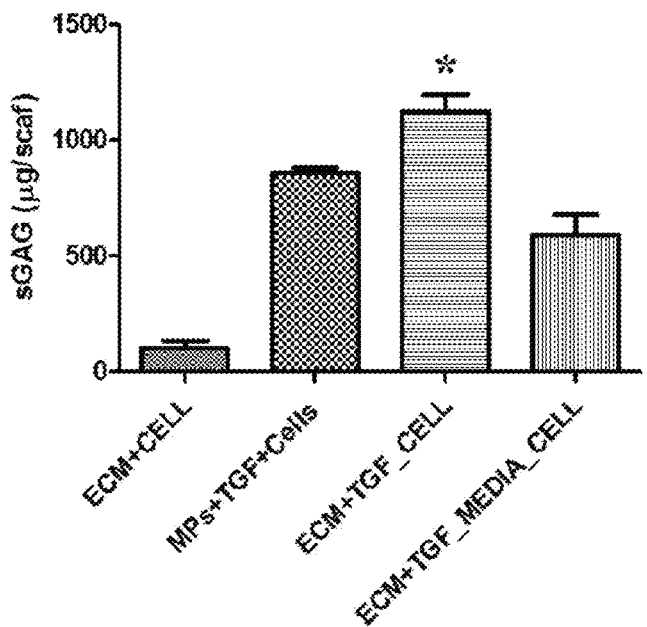
FIG. 13: GAG content of cartilage tissues engineered in vitro using ECM particle loaded hydrogels. Fibrin hydrogels containing ECM particles loaded with TGF-β3 showed higher GAG accumulation than constructs where TGF-β3 was either added directly to the media or added to control gelatine microparticles (MPs).
Figure 14:
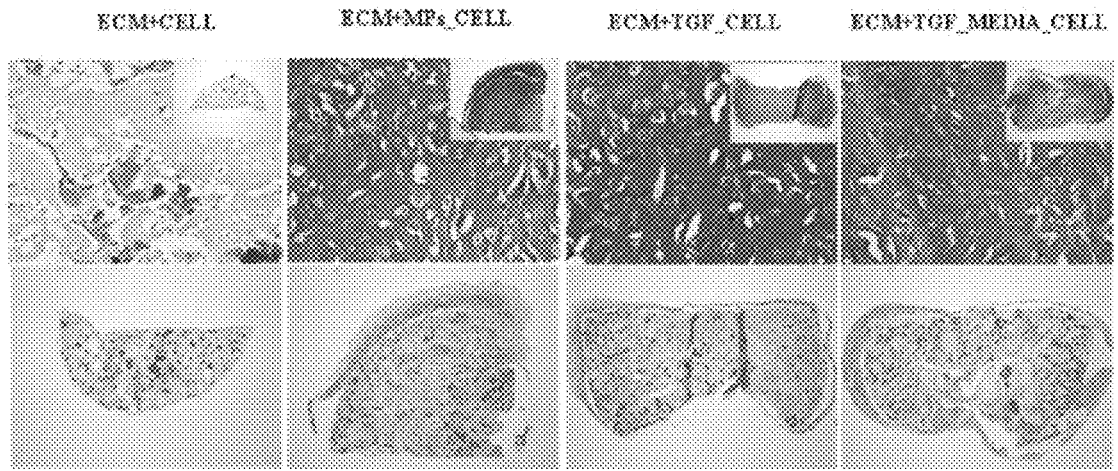
FIG. 14: Histology. GAG and Collagen staining of cartilage tissues engineered in vitro within fibrin hydrogels loaded with ECM derived particles
Figure 15:
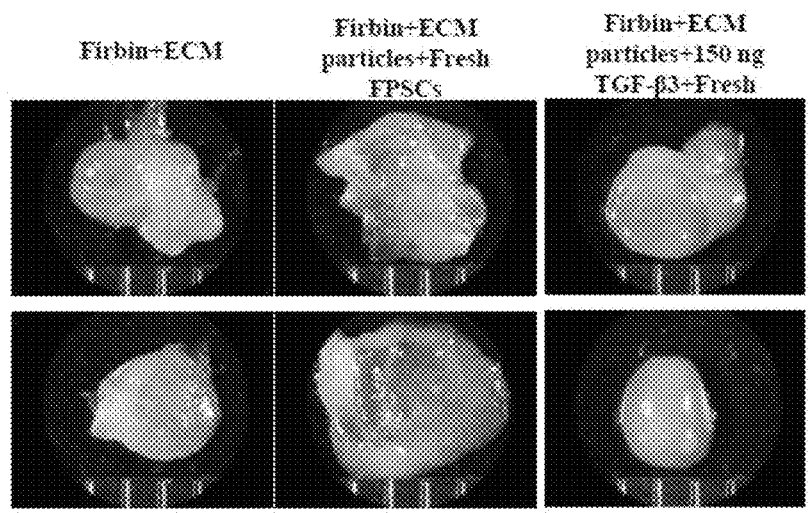
FIG. 15: Gross morphology after of tissues generated in vivo using proposed injectable construct.
Figure 16:
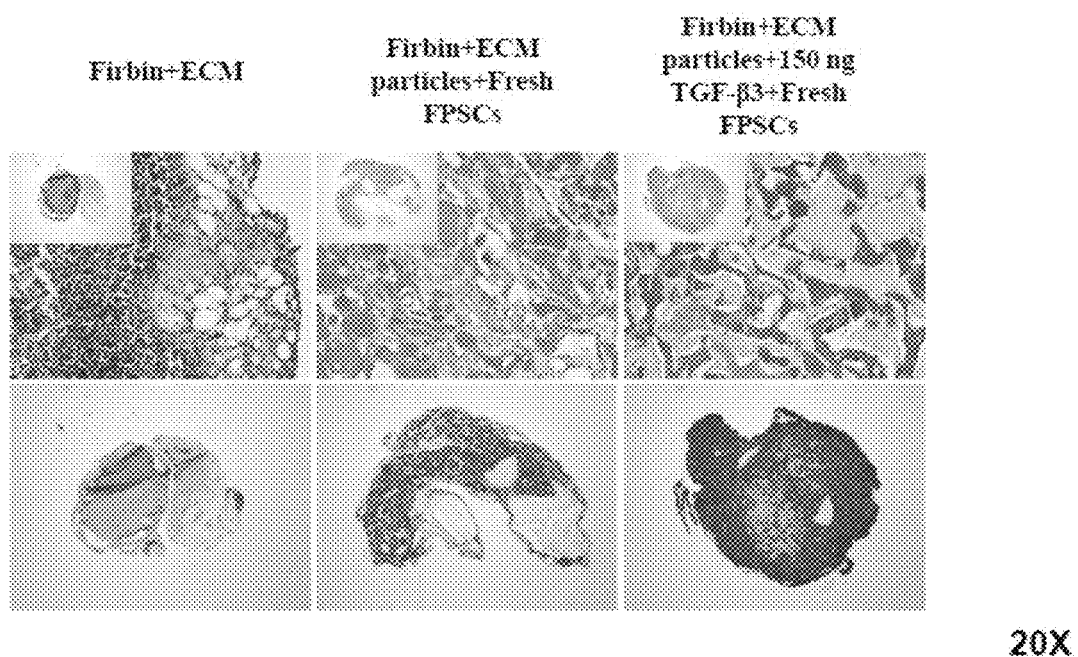
FIG. 16: Histology. GAG and Collagen staining for tissues generated in vivo.
Figure 17:
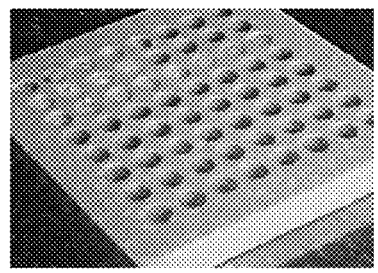
FIG. 17. A representative PDMS mould used to control freeze-drying of growth plate ECM to specific dimensions
Figure 18:
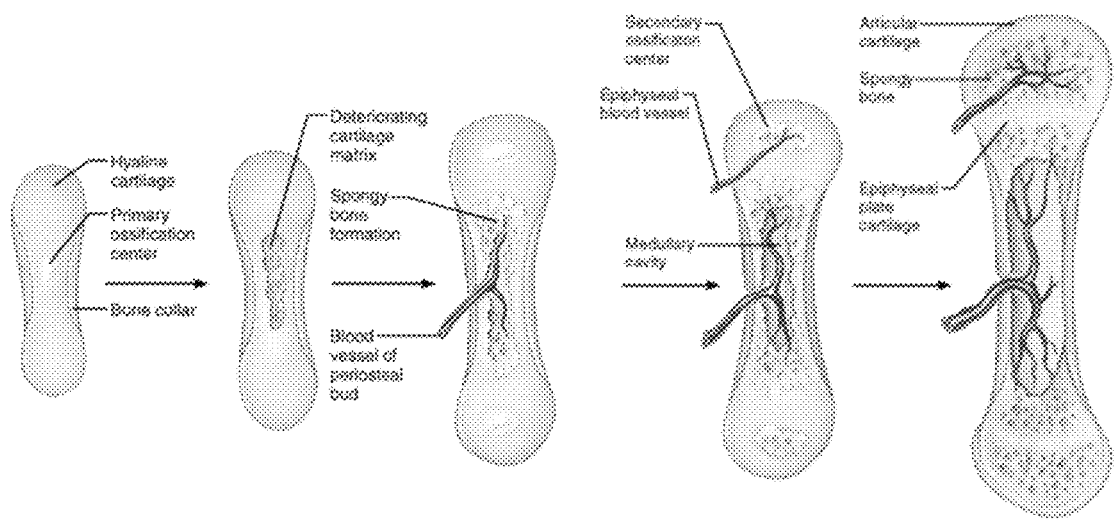
FIG. 18: Schematic outlining the steps involved in endochondral ossification, whereby a cartilage template is converted to a mature bone
Figure 19:
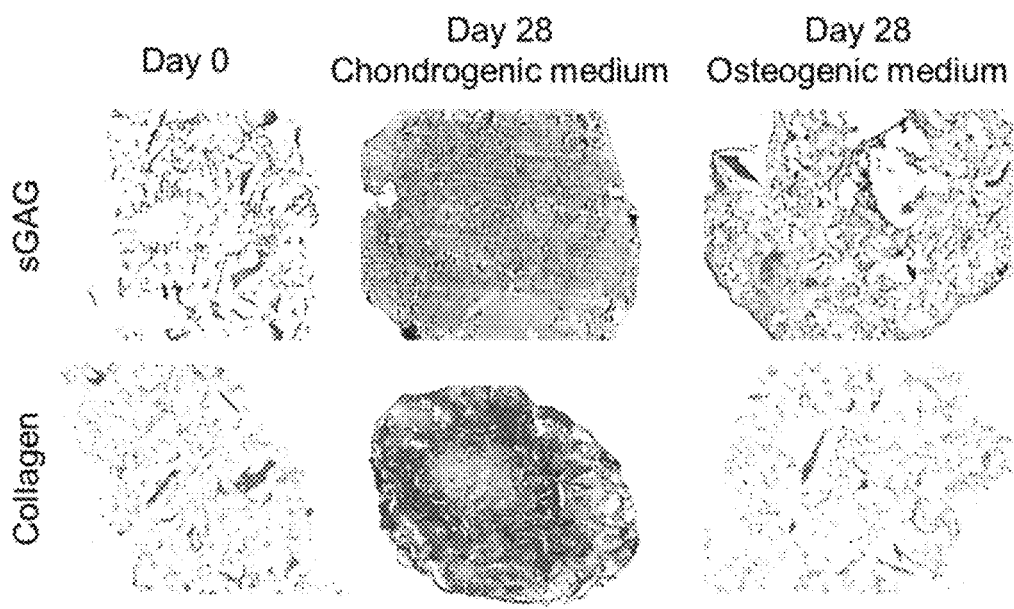
FIG. 19: Histological analysis of constructs at day 0 and following 28 days of culture in either chondrogenic or osteogenic medium, demonstrating the deposition of the main constituents of cartilage, sGAG and collagen.
Figure 20:
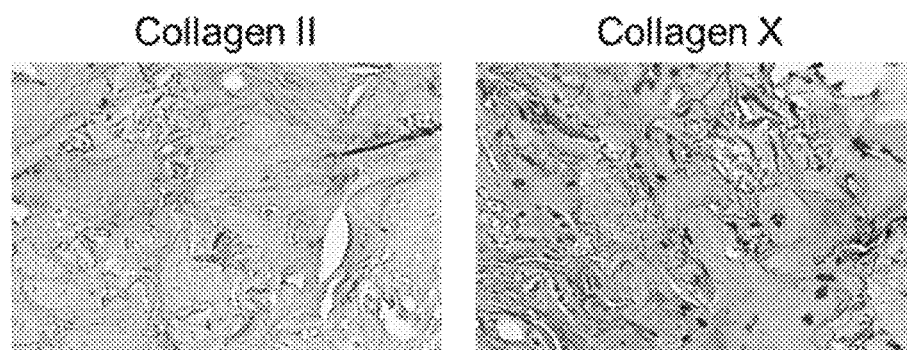
FIG. 20: MSC-seeded growth plate ECM constructs with positive collagen type II and collagen type X staining
Figure 21:
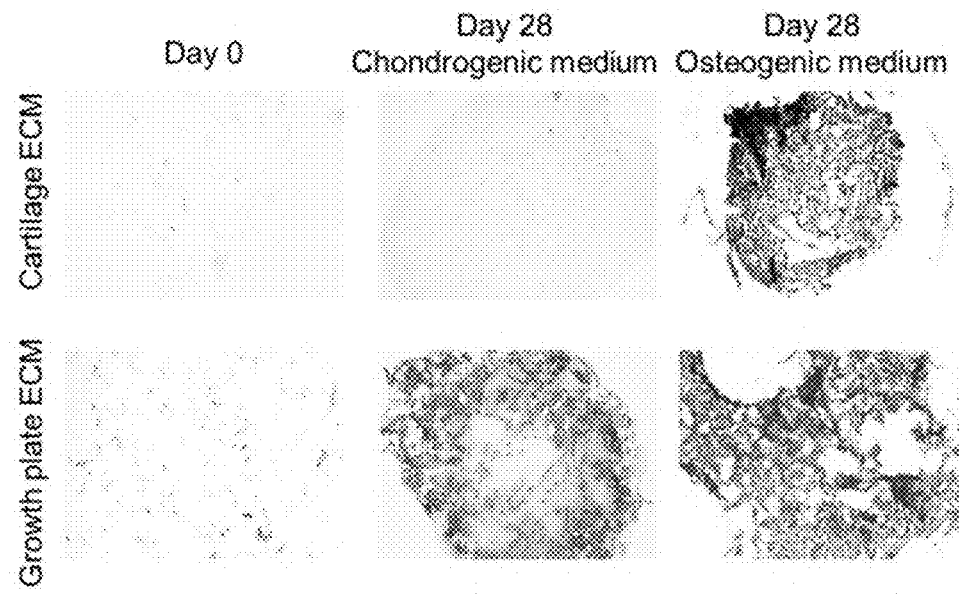
FIG. 21: Mineral deposition was observed in MSC-seeded growth plate ECM scaffolds cultured in either chondrogenic or osteogenic medium, in comparison to MSCs seeded on a cartilage ECM construct which only mineralised in osteogenic culture conditions.
Figure 22:
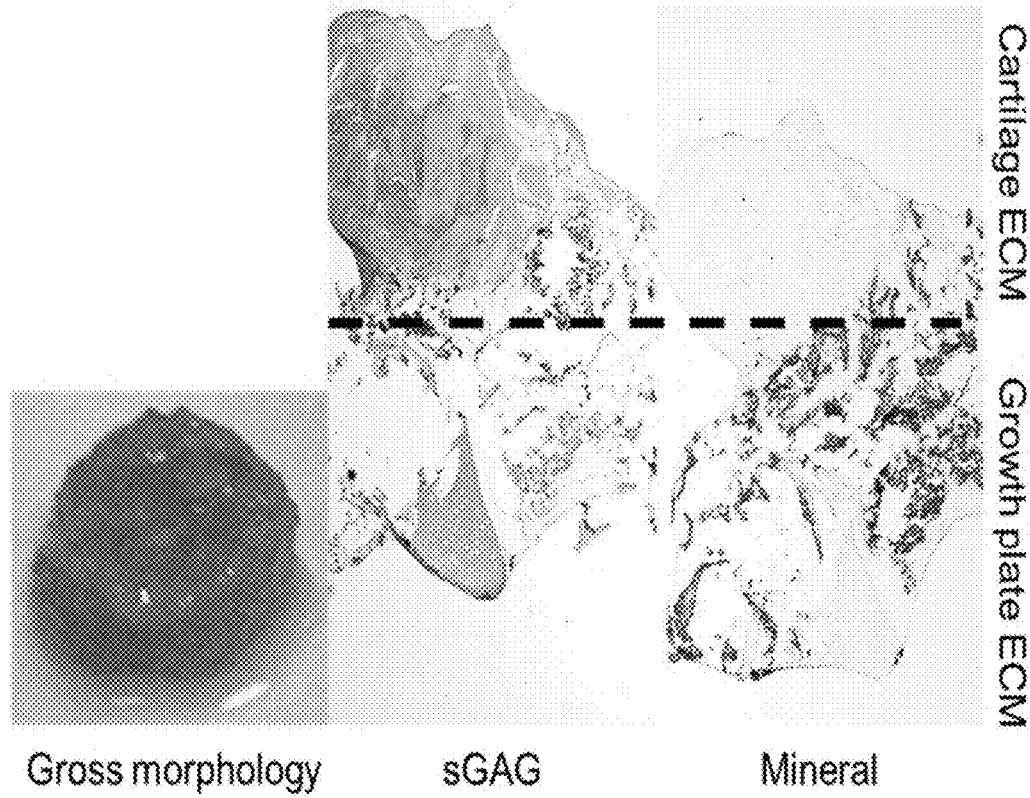
FIG. 22: An image of a bi-layered construct containing cartilage ECM in the top layer and growth plate ECM in the bottom layer and histological analysis of tissue deposited by MSCs seeded onto osteochondral scaffolds after 28 days in culture.
Figure 23:
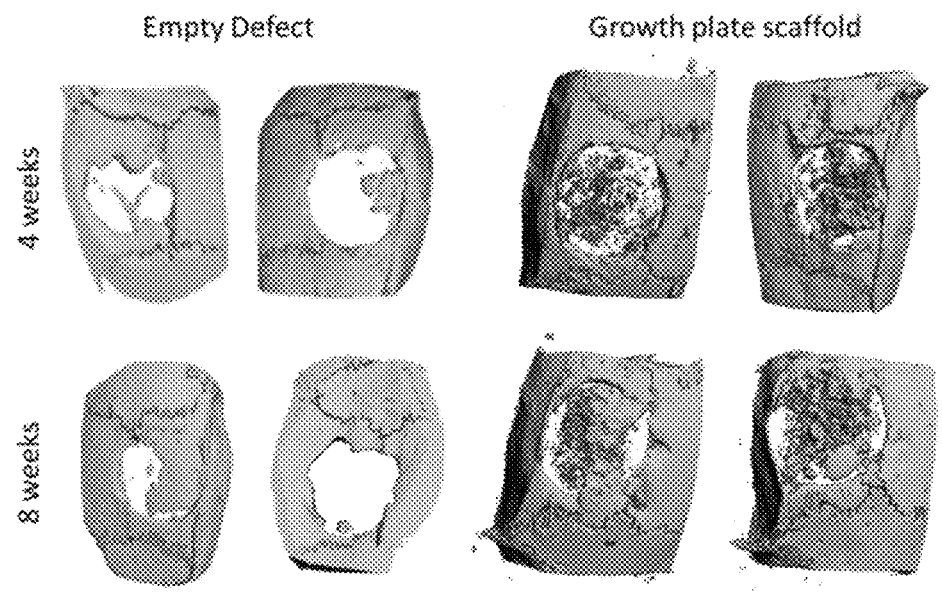
FIG. 23: Reconstructed images of growth plate scaffold treated and untreated cranial defects at 4 and 8 weeks showing the level of mineralisation achieved.
Figure 24:
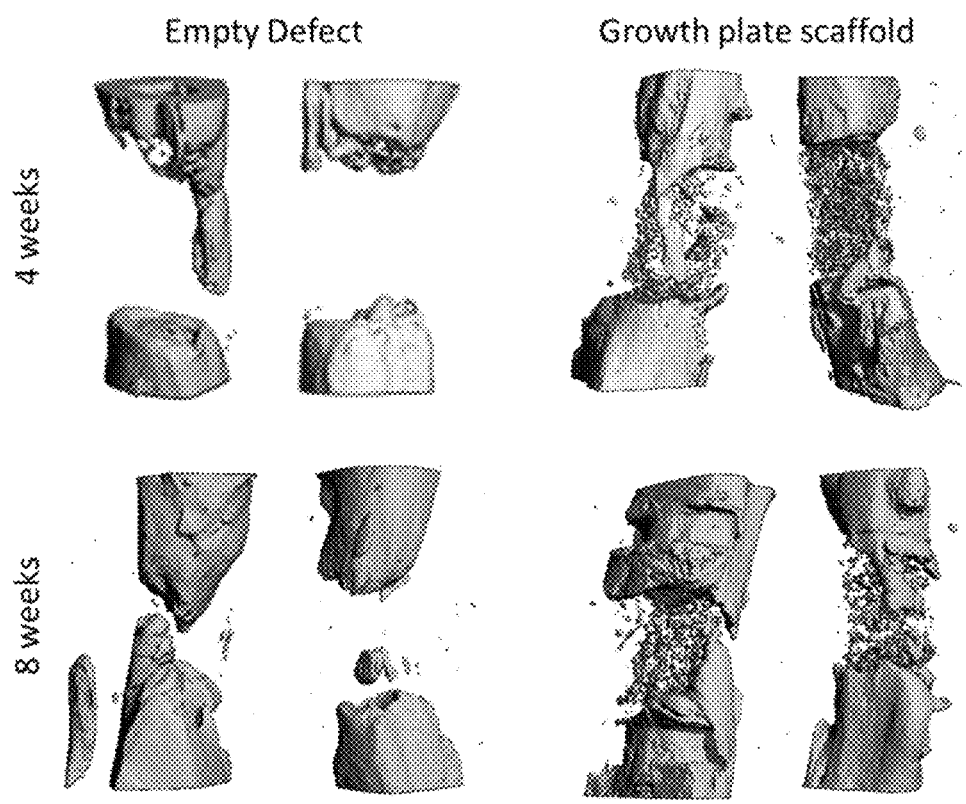
FIG. 24: Reconstructed images of growth plate scaffold treated and untreated femoral defects at 4 and 8 weeks showing the level of mineralisation achieved
Figure 25:
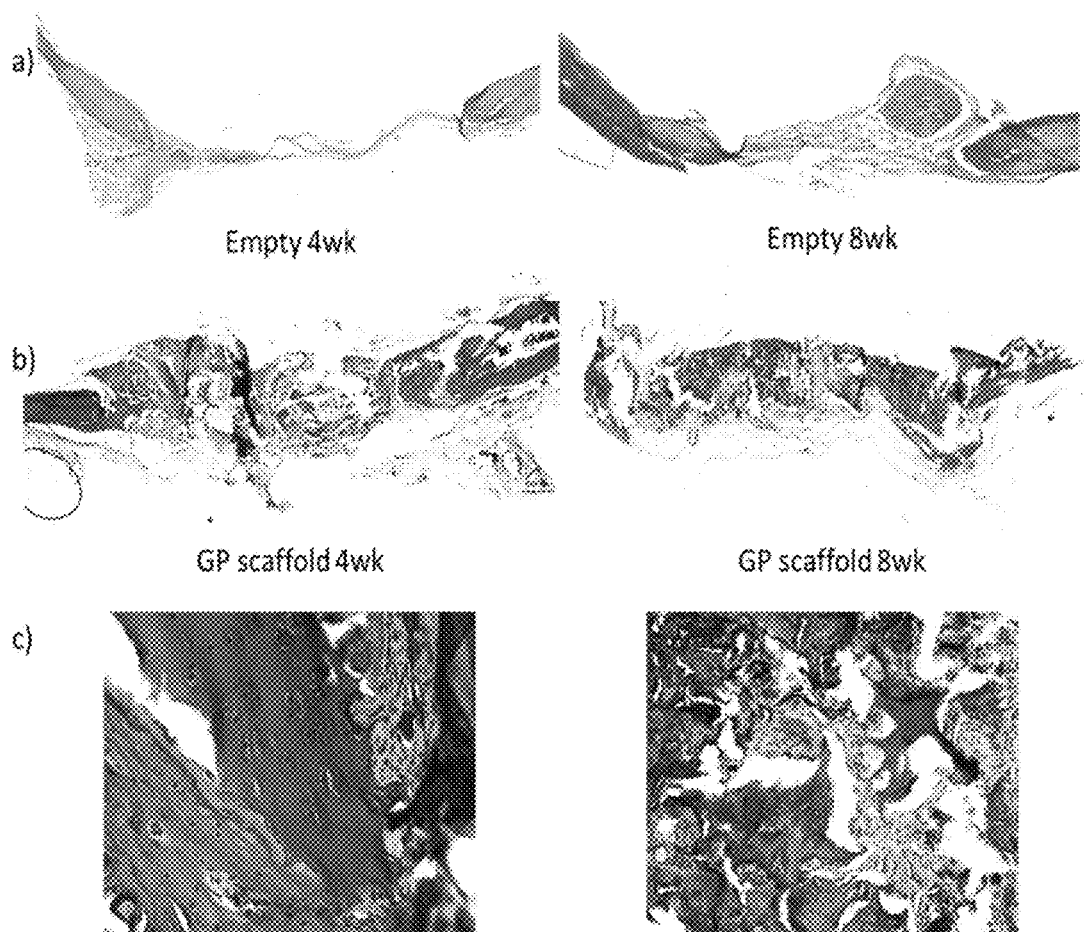
FIG. 25: Histological analysis of repair tissue formed across the cranial defect after 4 and 8 weeks either (a) untreated or (b) treated with the growth plate scaffold. (c) Higher power images of the repair tissue, demonstrating de novo bone forming both upon and within the original growth plate ECM tissue.
Figure 26:
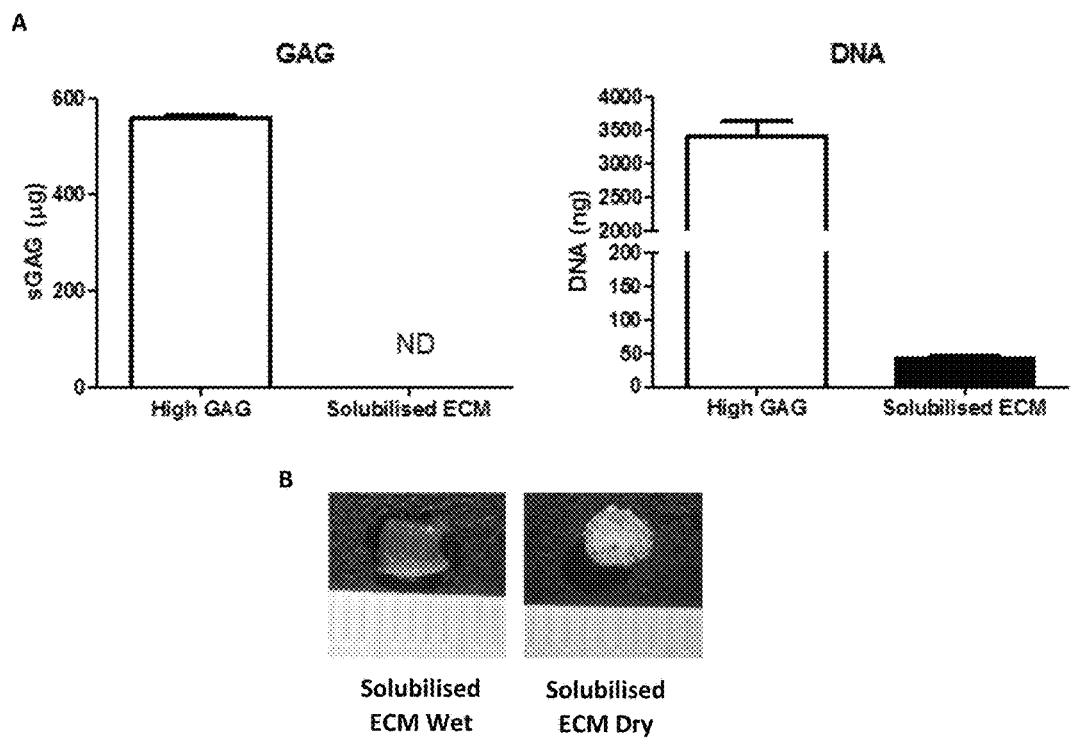
FIG. 26: Biochemical assays for DNA and GAG content of solubilised ECM scaffold (a). Scaffolds were generated using micronized ECM (High GAG) or solubilised ECM. Macroscopic images of wet and dry solubilised ECM scaffolds (b).
Figure 27:
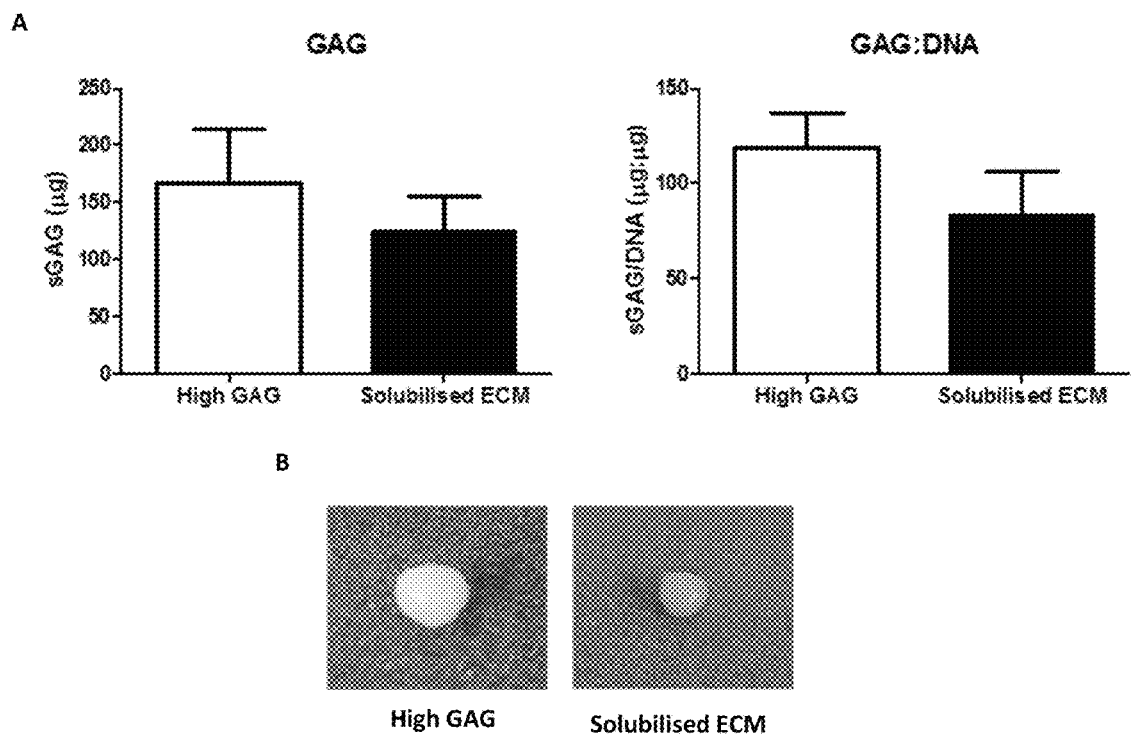
FIG. 27: Biochemical assays performed on cartilage tissues engineered in vitro using solubilised or micronized ECM scaffolds seeded with human stem cells (a). Scaffolds were generated using micronized ECM (High GAG) or solubilised ECM. Gross morphology of tissues generated using scaffolds (b).

In this specification, the term "porous" as applied to a scaffold should be understood to mean having a porosity of at least 90% as determined using the method of Gleeson et al (J. P. Gleeson, N. A. Plunkett, F. J. O'Brien—Addition of hydroxyapatite improves stiffness, interconnectivity and osteogenic potential of a highly porous collagen-based scaffold for bone tissue regeneration—Eur Cell Mater, 20 (2010), pp. 218-223) In one embodiment, the scaffold (or each layer in the scaffold) has a porosity of at least 91%, 92%, 93%, 94%, 95%, 96%, 97% or 98%. Ideally, the scaffold has a porosity of at least 98%, ideally at least 98.5%.

In this specification, the term "osseous defect" should be understood to mean any defect within bony tissue.

In this specification, the term "chondral defect" should be understood to mean any defect within the articular surface of a joint that does not penetrate through the subchondral bone.

In this specification, the term "osteochondral defect" should be understood to mean a defect to the articular surface that affects both the articular cartilage and the underlying bone.

In this specification, the term "extracellular matrix tissue" or "extracellular matrix" or "ECM" should be understood to mean a collection of extracellular molecules secreted by cells that provides structural and biochemical support to the surrounding cells. The ECM may be obtained from a mammal, for example a human or a non-human mammal, or it may be engineered in-vitro using published techniques, for example Vinardell et al (Vinardell, T., Sheehy, E., Buckley, C. T., Kelly, D. J. A comparison of the functionality and in vivo phenotypic stability of cartilaginous tissues engineered from different stem cells sources. Tissue Engineering Part A, 18(11-12), 1161-1170, 2012) and Buckley et al (Buckley, C. T., Vinardell, T., Kelly, D. J. Oxygen Tension Differentially Regulates the Functional Properties of Cartilaginous Tissues Engineered from Infrapatellar Fat Pad Derived MSCs and Articular Chondrocytes. Osteoarthritis and Cartilage, 18 (10), 1345-1354, 2010). Examples of extracellular matrix for the purpose of the present invention include cartilage ECM (obtained from porcine articular cartilage tissue) and growth plate. ECM (typically obtained from the epiphysial plate of porcine tibia or femora).

In this specification, the term "hyaline cartilage ECM" should be understood to mean ECM obtained from hyaline cartilage which is a tissue found, for example, in the ear and nose and on joint surfaces. It is mostly composed of type II collagen and chondroitin sulphate.

In this specification, the term "articular cartilage ECM" should be understood to mean ECM obtained from articular cartilage, which is a form of hyaline cartilage found at the articular end of joints.

In this specification, the term "growth plate ECM" or "growth plate tissue ECM" should be understood to mean ECM obtained from growth plate tissue of developing bones, typically developing long bones. This could include the epiphyseal plate in the metaphysis of a long bone, or articular cartilage from skeletally immature joints as this tissue is also known to act as a surface growth plate during development and skeletal maturation.

In this specification, the term "micronised" as applied to ECM should be understood to mean provided in a particulate form, in which the particles of ECM have a mean particle size of less than 200 microns as determined using routine light microscopy. Preferably, the micronised ECM has a mean particle size of less than 150 or 100 microns. Ideally, the micronized ECM has a mean particle size between 20 and 200 microns, 20 and 150 microns, 20 and 100 microns, 20 and 70 microns, 30 and 70 microns, 30 and 60 microns, 40 and 60 microns, and ideally about 50 microns. Methods of micronisation include milling, cryomilling, In this specification, the term "cryomilled" should be understood to mean a process in which a material is cryogenically frozen and then milled. Examples of cryomilling machines include the RETCH CRYOMILL™.

In this specification, the term "solubilised" should be understood to mean a process by which ECM tissue is digested, ideally enzymatically digested, to become soluble in an aqueous solvent. Suitably solubilising agents will be known to the person skilled in the art, and include enzymes and denaturing agents such as urea. An example of an enzyme that can be used to digest ECM tissue to become soluble is a protease, for example pepsin, or a collagenase. Preferably, the solubilised ECM will be a purified collagen with substantial removal of GAG and xenogeneic DNA. Ideally, the solubilised ECM will have greater than 50%, 60%, 70%, 80% or 90% removal of GAG and DNA when compared to native ECM tissue.

In this specification, the term "freeze-drying" as applied to a slurry refers to a process in which the slurry is frozen, typically to a final freezing temperature of from −10° C. to −70° C. and then sublimated under pressure. In one embodiment, the desired final freezing temperature is between −10° C. and −70° C. Suitably, the desired final freezing temperature is between −30° C. and −50° C. Typically, the desired final freezing temperature is between −35° C. and −45° C., ideally about −40° C. In one embodiment of the invention, freezing or freeze-drying is carried out at a constant cooling rate. This means that the rate of cooling does not vary by more than +/−10% of the target cooling rate, i.e. if the desired rate of cooling is 1.0° C./min, and the actual rate of cooling varied between 0.9° C./min and 1.1° C./min, this would nonetheless still be considered to be a constant cooling rate. Typically, the constant cooling rate is between 0.1° C./min to 10° C./min. Preferably, freeze-drying is carried out at a constant cooling rate of between 0.5° C./min to 1.5° C./min. More preferably, freezing or freeze-drying is carried out at a constant cooling rate of between 0.8° C./min to 1.1° C./min. Typically, freezing or freeze-drying is carried at a constant cooling rate of about 0.9° C./min. The temperature of the freeze-drying chamber at a start of the freeze-drying process (i.e. when the slurry is placed in the chamber) is usually greater than 0° C., preferably at about ambient temperature. The sublimation step is generally carried out after the final freezing temperature is reached. This step involves heating the freeze-drying chamber to a sublimation temperature (generally about 0° C.), preferably at a constant heating rate. The process typically includes a final sublimation step where an ice phase in the formed scaffold is sublimated under vacuum for a suitable period of time.

In this specification, the term "slurry" should be understood to mean a suspension of micronized ECM in a solvent, suitably an aqueous solvent, for example water. Typically, the slurry comprises less than 500, 400, 300 mg/ml micronized ECM. Suitably, the slurry comprises 100-500, 100-400, 200-300, 230-270, and ideally about 250 mg/ml micronized ECM.

In this specification, the term "cross-linked" should be understood to mean treated to introduce cross-links between different polymeric molecules in the ECM. The ECM may be micronised ECM or solubilised ECM. Crosslinking may be performed on the solubilised ECM or on the formed freeze-dried scaffold. Typically, the scaffold is cross-linked by one or more of the means selected from the group comprising: dehydrothermal (DHT) cross-linking; and chemical cross-linking. When crosslinking is be performed on the solubilised ECM, the crosslinking agent is typically a chemically crosslinking agent. Suitable chemical cross-linking agents and methods will be well known to those skilled in the art and include a glyoxal, 1-Ethyl-3-[3-dimethylaminopropyl]carbodiimide hydrochloride (EDAC) or Glutaraldehyde. Ideally, the scaffold is cross-linked using DHT and EDAC cross-linking. Cross-linking can be carried out at any stage of the fabrication process. In a preferred embodiment, scaffold pore symmetry can be controlled by varying the degree of cross-linking within each respective layer using cross linking methods familiar to one skilled in the art. Similarly, in another embodiment, scaffold permeability or flow conductivity can be varied by varying the mechanical properties of the scaffold using either cross linking or other stiffness improvement methodologies known to one skilled in the art.

In this specification, the term "GAG" should be understood to mean glycosaminoglycan, particularly sulphated glycosaminoglycans.

In this specification, the term "reduced GAG content" as applied to ECM from a given source should be understood to mean a GAG content that is reduced compared to natural ECM from the same source, for example less than 90%, 80%, 70%, 60%, 50%, 40%, 30%, 20%, 10% or 5% GAG content of natural ECM. Methods of reducing GAG content include the use of buffers, detergents (such as Sodium dodecyl sulfate or Triton-X or Sodium deoxycholate) or other chemicals (e.g. chondroitinase ABC) known to reduce the sGAG content of tissues.

In this specification, the term "decellularised" or "devitalised" as a applied to a material (for example ECM, a scaffold, or a gel) should be understood to mean that the cellular content of the material is reduced partially or preferably completely. Method of decellularising a material include chemical nucleic acid digestion, possibly following partial or total removal of matrix components from the ECM.

In this specification, the term "seeding" as applied to a scaffold should be understood to mean incorporating a biological material into a scaffold. Method of seeding a scaffold include soaking the scaffold in a solution containing the biological material for a sufficient time to allow the biological material infiltrate the pores of the scaffold.

In this specification, the term "cells" should be understood to mean any type of cell, particularly stem cells, chondrocytes, and osteoblasts. Preferably, the cells are mesenchymal stem cells.

In this specification, the term "biological material" should be understood to mean proteins, peptides, nucleic acid, nucleic acid constructs, nucleic acid vectors, or chemical molecules having biological activity. Preferably, the biological material comprises a biological growth factor, for example one or more of the TGF-β superfamily, (IFG, FGF, BMP, PDGF, EGF) or cannabinoids.

In this specification, the term "cannabinoids" should be understood to mean a biological compound which can be naturally or synthetically derived and that acts on the cannabinoid receptor types 1 and/or 2 ($CB_1$ and $CB_2$), for example Δ 9-tetrahydrocannabinol (Δ 9-THC).

In this specification, the term "gel base" should be understood to mean a matrix having both solid and liquid properties. An exemplary gel base is an agarose gel.

In this specification, the term "injectable" should be understood to mean that the gel is sufficiently deformable to enable it to be injected into a defect in cartilage or bone.

EXPERIMENTAL

Development of Decellularized ECM Derived Scaffolds with a Uniform Pore Size.

Cartilage used in the fabrication of ECM derived scaffolds was harvested, in sterile conditions, from the femoral condyles of female pigs (3 months old) shortly after sacrifice. The cartilage was first broken up into small pieces using a scalpel. Cartilage particles were then broken up using a cryogenic mill (6770 Freezer/Mill, SPEX, UK). These small pieces of cartilage where then homogenized in distilled water (dH2O) using a homogenizer (IKAT10, IKA Works Inc, NC, USA) to create a cartilage slurry (250 mg/ml). The slurry was transferred to custom made moulds (containing wells 5 mm in diameter and 3 mm in height) and freeze-dried (FreeZone Triad, Labconco, KC, USA) to produce porous scaffolds. Briefly, the slurry was frozen to −30° C. (1° C./min) and kept at that temperature for one hour. The temperature was then increased to −10° C. (1° C./min), followed by a hold of 24 hours and then finally increased to room temperature (0.5° C./min). Next, two different cross-linking techniques were applied to the scaffolds. The scaffolds underwent DHT and 1-Ethyl-3-3dimethyl aminopropyl carbodiimide (EDAC) crosslinking. The DHT process was performed in a vacuum oven (VD23, Binder, Germany), at 115° C., in 2 mbar for 24 hours. The EDAC (Sigma-Aldrich, Germany) crosslinking consisted of chemical exposure for 2 hours at a concentration of 6 mM in the presence of N-Hydroxysuccinimide (NETS) (Sigma-Aldrich, Germany). A molar ratio of 2.5 M EDAC/M N-Hydroxysuccinimide was used. After EDAC crosslinking the scaffolds were washed twice in sterile PBS (Sigma-Aldrich, Germany).

Development of Decellularized ECM Derived Scaffolds with Controlled Pore Size and Tailored Growth Factor Release Rates.

Articular cartilage was harvested from femoral condyles of female 4 months old pigs under sterile condition shortly after sacrifice. All steps of the decellularization and tailoring GAG protocol were performed in 2 mL working volume at room temperature. This protocol consists of three phases. In Phase I, the 50 and 5% GAG groups were incubated in basic buffer (10 mM Tris-HCl (pH 8.0)) containing 100 mM DTT, 2 mM MgCl2, and 10 mM KCl for 24 hrs; and anatomically adjacent pieces of cartilage subjected to 1 min incubations for 100% GAG group. The 5% GAG groups were additionally subjected to 0.5 SDS treatment with basic buffer containing 100 mM DTT, 2 mM MgCl2, and 10 mM KCl for 24 hrs. Following sGAG removal, nucleic acid digestion (2.5 Kunitz units/mL deoxyribonuclease I, 7.5 Kunitz units/mL ribonuclease A, 0.15 M NaCl, 2 mM MgCl2 (H2O) in 10 mM Tris-HCl (pH 7.6)) was performed for 24 h and washout (10 mM Tris-buffered saline (pH 7.5)) for 48 h. In phase II, the cartilage tailored GAG-ECM scaffolds were prepared by cryo-milling followed by DHT+EDAC crosslinking as described in section 1 above.

Development of Solubilised ECM Derived Scaffolds

Cartilage used in the fabrication of ECM derived scaffolds was harvested, in sterile conditions, from the femoral condyles or growth plates of female pigs (3 months old) shortly after sacrifice. The cartilage was first broken up into small pieces using a scalpel. ECM tissue was then transfer to sterile containers. ECM tissue was then pre-treated with 0.2M NaOH for 24 hours at 4° C. After washing and removal of pre-treatment solution, the ECM tissue was then digested with pepsin in 0.5 M Acetic Acid. Pepsin is added at a concentration of ~1500 units pepsin per 50 mg ECM tissue. The ECM was then incubated in the pepsin solution for 24 hours at <20° C. with rotation at a speed of 4 rpm. Salt precipitation was then performed to extract purified collagen using concentration of NaCl between 0.1M-5M. In order to remove any remaining salt, acid or pepsin, dialysis can be performed on the solubilised collagen. Dialysis was performed against 0.02 M $Na_2HPO_4$ (pH 9.4) for 24 h at 4° C. The solubilised collagen can then be freeze-dried. To generate scaffolds, the freeze dried collagen was rehydrated in an aqueous solution at a concentration range of 1 mg/ml to 200 mg/ml preferably, 20 mg/ml. Once rehydrated the collagen can then be cross-linked to form a gel with Glyoxal at a concentration between 1 mM and 50 mM preferably, 10 mM. The solution is then incubated for 30 minutes at 37° C. to allow cross-linking to take place. After incubation the gel can then be transferred to moulds and freeze-dried to create scaffolds.

Development of Injectable Decellularized ECM Derived Particles as Growth Factor Delivery Systems.

Particulated cartilage ECM is fabricated as described in 1 or 2 above. Instead of freeze-drying these particles to produce a porous scaffold, it is also possible to combine these particles with a hydrogel to develop an injectable chondroinductive composite biomaterial that also acts as a growth factor delivery system.

One manifestation of this invention would be to combine ECM particles with a fibrin hydrogel. The particulated cartilaginous material is incorporated into the hydrogel by mixing directly with the fibrinogen, with the desired ratio. Gelation occurs by adding thrombin to the fibrinogen/ECM-particles slurry. Appropriate mixing ensures a homogeneous distribution of bioactive cartilage ECM-derived micro-particles within the hydrogel.

Development of Decellularized Growth Plate ECM Derived Scaffolds.

Growth plate used in the fabrication of ECM derived scaffolds was harvested, in sterile conditions, from the femur, fibula and tibia of female pigs (3 months old) shortly after sacrifice. The growth plate was first broken up into small pieces using a scalpel, and then broken up using a cryogenic mill (6770 Freezer/Mill, SPEX, UK). These small pieces of growth plate were then homogenized in distilled water ($dH_2O$) using a homogenizer (IKAT10, IKA Works Inc, NC, USA) to create a slurry (250 mg/ml). The slurry was transferred to custom made moulds and freeze-dried (FreeZone Triad, Labconco, KC, USA) to produce porous scaffolds. Briefly, the slurry was frozen to −30° C. (1° C./min) and kept at that temperature for one hour. The temperature was then increased to −10° C. (1° C./min), followed by a hold of 24 hours and then finally increased to room temperature (0.5° C./min). Next, two different cross-linking techniques were applied to the scaffolds. The scaffolds underwent DHT and 1-Ethyl-3-3dimethyl aminopropyl carbodiimide (EDAC) crosslinking. The DHT process was performed in a vacuum oven (VD23, Binder, Germany), at 115° C., in 2 mbar for 24 hours. The EDAC (Sigma-Aldrich, Germany) crosslinking consisted of chemical exposure for 2 hours at a concentration of 6 mM in the presence of N-Hydroxysuccinimide (NHS) (Sigma-Aldrich, Germany). A molar ratio of 2.5 M EDAC/M N-Hydroxysuccinimide was used. After EDAC crosslinking the scaffolds were washed twice in sterile PBS (Sigma-Aldrich, Germany).

Results obtained from both in vitro and in vivo characterisation of the growth plate scaffold will be presented below, and demonstrate its potential for use in bone tissue regeneration. Also, we will display the ability of the growth plate scaffold layer to be combined with a cartilage ECM layer to generate an osteochondral graft which can be potentially applied to repair both bone (osteo) and cartilage (chondral) layers simultaneously.

The invention is not limited to the embodiments hereinbefore described which may be varied in construction and detail without departing from the spirit of the invention.

The invention claimed is:

1. A method for making a porous scaffold suitable for use in repair of osseous, chondral, or osteochondral defects in a mammal, the method comprising the steps of:
    A) providing a gel comprising solubilized extracellular matrix (ECM) tissue;
    B) chemically crosslinking the extracellular matrix (ECM) tissue utilizing glyoxal as the chemically crosslinking agent;
    C) freeze-drying the gel to provide the porous scaffold;
    D) dehydrothermally (DHT) crosslinking the scaffold to produce a first layer; and
    E) repeating steps A-D to make a second layer, wherein the first layer is attached to the second layer;
    wherein the extracellular matrix is treated to reduce the GAG content to less than 90% of the GAG content of untreated ECM, and wherein the ECM tissue in at least one layer is cartilage ECM.

2. The method according to claim 1, in which the ECM is solubilized by enzymatic digestion.

3. The method according to claim 1, in which the ECM is micronized prior to solubilization.

4. The method according to claim 3, in which the micronized cartilage extracellular matrix tissue has a mean particle size of 10-200 microns.

5. The method according to claim 1, in which the cartilage ECM is hyaline cartilage ECM or growth plate ECM.

6. The method according to claim 3, in which the cartilage ECM is decellularised before or after micronizing.

7. The method according to claim 1, in which the method of the invention includes an additional step of seeding the scaffold with a biological material selected from the group consisting of: cells and a biological growth factor.

8. The method according to claim 7, in which the cells are selected from the group consisting of: stem cells, chondrocytes, mesenchymal cells and osteoblasts; and/or
    in which the biological growth factor is selected from the group consisting of: one or more of the TGF-β superfamily or cannabinoids.

9. The method according to claim 1, in which the method further comprises a step of attaching the first layer to the second layer to form the multilayer scaffold, in which the first layer comprises hyaline cartilage ECM and the second layer comprises growth plate ECM.

10. A multilayer scaffold suitable for repair of osteochondral defects in a mammal and having a first layer comprising a porous scaffold according to claim 1 in which the cartilage ECM is hyaline cartilage ECM and a second layer comprising a porous scaffold according to claim 1 in which the cartilage ECM is growth plate ECM, in which the first layer is attached to the second layer.

11. The method according to claim 1, in which the cartilage ECM is broken up and treated with a basic solution to reduce the GAG content to less than 90% of the GAG content of untreated ECM.

12. The method according to claim 11, wherein the basic solution comprises a sodium hydroxide solution.

13. The method of claim 1, wherein the extracellular matrix is treated to reduce the GAG content to 5% or less of the GAG content of untreated ECM.

14. The method according to claim 1, wherein the gel comprises solubilized ECM at a concentration range of 1 mg/ml to 200 mg/ml in an aqueous solution cross-linked with the glyoxal at a concentration range of 1 mM to 50 mM.

15. The method according to claim 14, wherein the gel comprises solubilized ECM at a concentration of 20 mg/ml.

16. The method according to claim 14, wherein the gel comprises solubilized ECM at a concentration of 10 mg/ml.

17. The method according to claim 14, wherein the solubilized ECM is cross-linked with the glyoxal at a concentration of 10 mM.

18. The method according to claim 1, in which the cartilage ECM is articular cartilage ECM.

19. A method for making a porous scaffold suitable for use in repair of osseous, chondral, or osteochondral defects in a mammal, the method comprising the steps of:
    A) providing a gel comprising a least a first layer of solubilized extracellular matrix (ECM) tissue and a second layer of solubilized ECM tissue;
    B) chemically crosslinking the extracellular matrix (ECM) tissue utilizing glyoxal as the chemically crosslinking agent;
    C) freeze-drying the gel to provide the porous scaffold;
    D) dehydrothermally (DHT) crosslinking the scaffold;
    wherein the extracellular matrix is treated to reduce the GAG content to less than 90% of the GAG content of untreated ECM, and wherein the ECM tissue in at least one layer is cartilage ECM.

* * * * *